United States Patent
Romero Amaya et al.

(10) Patent No.: US 7,666,254 B1
(45) Date of Patent: Feb. 23, 2010

(54) BORATE COMPOSITIONS FOR WOOD PRESERVATION

(75) Inventors: Francisco Javier Romero Amaya, Peachtree City, GA (US); Jun Zhang, Getzville, NY (US)

(73) Assignee: Osmose, Inc., Buffalo, NY (US)

( * ) Notice: Subject to any disclaimer, the term of this patent is extended or adjusted under 35 U.S.C. 154(b) by 242 days.

(21) Appl. No.: 11/894,373

(22) Filed: Aug. 20, 2007

Related U.S. Application Data

(60) Provisional application No. 60/822,793, filed on Aug. 18, 2006.

(51) Int. Cl.
*A01N 59/14* (2006.01)
*A01N 53/00* (2006.01)

(52) U.S. Cl. ............... 106/18.3; 106/15.05; 106/18.29; 106/18.35; 424/657; 424/658; 424/659; 424/660; 427/297; 427/397; 428/537.1; 514/730; 514/772

(58) Field of Classification Search .............. 106/15.05, 106/18.3, 18.29, 18.35; 424/657, 658, 659, 424/660; 428/537.1; 427/297, 397; 514/730, 514/772

See application file for complete search history.

(56) References Cited

U.S. PATENT DOCUMENTS

| | | | | |
|---|---|---|---|---|
| 5,874,025 | A * | 2/1999 | Heuer et al. | 252/383 |
| 6,753,016 | B2 * | 6/2004 | Ghosh | 424/604 |
| 7,426,948 | B2 * | 9/2008 | Richardson et al. | 144/364 |
| 2003/0086979 | A1 * | 5/2003 | Ghosh | 424/600 |
| 2004/0258767 | A1 * | 12/2004 | Leach et al. | 424/630 |
| 2005/0118280 | A1 * | 6/2005 | Leach et al. | 424/617 |
| 2005/0255251 | A1 * | 11/2005 | Hodge et al. | 427/397 |
| 2006/0086284 | A1 * | 4/2006 | Zhang et al. | 106/15.05 |
| 2006/0112850 | A1 * | 6/2006 | Zhang et al. | 106/15.05 |
| 2006/0127432 | A1 * | 6/2006 | Romero Amaya | 424/405 |
| 2006/0257578 | A1 * | 11/2006 | Zhang et al. | 427/393.3 |
| 2006/0288904 | A1 * | 12/2006 | Leach et al. | 106/15.05 |
| 2007/0021385 | A1 * | 1/2007 | Zhang et al. | 514/63 |
| 2007/0074640 | A1 * | 4/2007 | Romero Amaya et al. | 106/160.1 |
| 2007/0131136 | A1 * | 6/2007 | Zhang et al. | 106/15.05 |
| 2008/0175913 | A1 * | 7/2008 | Zhang et al. | 424/489 |
| 2008/0193640 | A1 * | 8/2008 | Zhang et al. | 427/140 |
| 2008/0260841 | A1 * | 10/2008 | Leach et al. | 424/489 |
| 2009/0028917 | A1 * | 1/2009 | Leach et al. | 424/409 |
| 2009/0035564 | A1 * | 2/2009 | Leach et al. | 428/338 |

FOREIGN PATENT DOCUMENTS

WO WO2004/050783 A1 * 6/2004

OTHER PUBLICATIONS

Superior Court of New Jersey, Decision After Trial, *Phibro-Tech, Inc. v. Osmose Holding, Inc.*, Jun. 25, 2007.
Superior Court of New Jersey Chancery Division, Final Judgment, *Phibro-Tech, Inc. v. Osmose Holdings, Inc., Osmose, Inc.*, Aug. 14, 2007.

* cited by examiner

*Primary Examiner*—Anthony J Green
(74) *Attorney, Agent, or Firm*—Milbank, Tweed, Hadley, Hadley & McCloy LLP

(57) ABSTRACT

A wood preservation composition comprising an unexpectedly efficacious combination of a boron compound and bifenthrin is disclosed. A method of preserving wood, as well as the preserved wood, are also disclosed.

31 Claims, 1 Drawing Sheet
(1 of 1 Drawing Sheet(s) Filed in Color)

BORATE COMPOSITIONS FOR WOOD PRESERVATION

CROSS-REFERENCE TO RELATED APPLICATION

This application claims priority of U.S. Provisional Application No. 60/822,793, filed on Aug. 18, 2006, and the disclosure of which is incorporated herein by reference.

BACKGROUND OF THE INVENTION

Boron compounds have long been used in the wood preservation industry for the preservation of wood from termite attack. However, many boron compounds have a degree of solubility in water such that upon exposure of treated wood to environmental conditions, the compound can, under some conditions, leach from the wood, causing wood treated with boron compounds to demonstrate a preservation efficacy which is less than would be expected from the calculated retention immediately following treatment with the compound. For example, wood which has been exposed to damp environments is known to suffer from a reduced preservation efficacy, possibly due to leaching of the boron compound to the environment.

SUMMARY OF THE INVENTION

A wood preservation composition comprising an unexpectedly efficacious combination of a boron compound and bifenthrin is disclosed. A method of preserving wood, as well as the preserved wood, are also disclosed.

BRIEF DESCRIPTION OF THE DRAWING

The patent or application file contains at least one drawing executed in color. Copies of this patent or patent application publication with color drawing(s) will be provided by the Office upon request and payment of the necessary fee.

FIG. 1 shows a test specimen being exposed to *C. acinaciformis*.

DESCRIPTION OF THE INVENTION

Under some conditions, the effect mentioned in the background can be pronounced enough such that the wood preservation efficacy at high BAE (boric acid equivalent) retentions can be less than that at lower BAE retentions. For example, under some conditions, wood treated to BAE retentions of about 0.5 wt % have demonstrated a significantly lower resistance to termite attack over time than wood treated to retentions of 0.2 or 0.1 wt %. It has been found that under some conditions, the combination of certain boron compounds, such as disodium octaborate, and bifenthrin, each used at concentrations near their individual maximum effectiveness, has an efficacy which is greater than that of bifenthrin alone. This is surprising because the peak effectiveness of bifenthrin is much greater than that of disodium octaborate, and one would expect that the sum effectiveness of the two when used at or near the peak effectiveness of each would be equal to the peak effectiveness of bifenthrin. Instead that the sum effectiveness of the two is greater. Furthermore, the effect is still manifest even when conditions are such that the disodium octaborate effectiveness alone actually decreases with increasing concentration. Over a range of retentions from about 0.15 to about 7.0 wt % BAE, the combination of disodium octaborate with bifenthrin at retentions above about 0.2 grams per cubic meter of wood gives a protection which steadily increases with wt % BAE retention, even at conditions which are such that the disodium octaborate efficacy in the absence of bifenthrin does not increase with increasing concentration.

Provided is a wood preservative composition comprising a borate compound and bifenthrin. The compositions can be manufactured, transported, stored and used as one concentrated product or several concentrated products that are diluted at the treatment plant or place of use to produce working solutions that are applied to wood. Additionally, or alternatively, the compositions can be manufactured in diluted ready-to-use form. The compositions can be used for protection of wood and other cellulosic and natural fiber materials against biodeterioration. The biodeterioration may be caused by agents including mold, fungi, insects and termites.

Also provided is a method of preserving wood and other cellulosic materials, as well as wood and other cellulosic materials preserved with the composition. The composition can be applied to the following cellulosic material including but not restricted to wood and wood products such as lumber, framing lumber, plywood, sill plates, oriented strand board and I-joists. It can also be useful for pre-building treatment for houses and other buildings. Other non-limiting applications in which the wood preservative composition of the present invention can be used include wood composites, including but not limited to Oriented Strand Board (OSB), flakeboards, particleboards, medium density fibre boards (MDF); engineering wood products including but not limited to plywood, laminated veneer lumber (LVL), glue laminated lumber (GluLam), 1-joist and any other veneer based composites; solid wood; wood-plastic composites, plastic composites containing cellulose or cellulosic materials coming from wood or other sources and combinations of these products. Examples of natural fibers which can be treated with the composition of the present invention include fibers from rice, wheat, sugar cane, bamboo, or fiber derived from tree bark.

The wood preservative formulation of the present invention can be applied as a concentrate or in diluted form during or after the manufacturing of the wood, wood composite, cellulosic or natural fiber product as described in this invention. The wood preservative formulations can also be applied when the cellulosic material, wood composite or plastic wood composite or products described in this invention are in service. The composition can be applied to or incorporated into the product by methods including but not limited to the following: addition of the composition into manufacturing or other production of raw materials, addition of the composition into the manufacturing of products made from raw materials which may or may not be treated with the composition; glue line addition, spray-on, dip or brush-on, vacuum, vacuum pressure or a combination of the foregoing processes, all of which may be used in, for example, building construction applications. Preferred are vacuum and vacuum pressure methods.

The retention of the boron compound in the wood or wood product is in the range of from 0.1 to 0.8, expressed as wt % Boric Acid Equivalent (BAE), and in other embodiments, is in the range of from 0.15 to 0.7 wt % BAE, 0.18 to 0.7 wt % BAE, and 0.20 to 0.7 wt % BAE. In further embodiments, the wt % BAE is in the range of from about 0.25, 0.30, 0.35, 0.40, 0.45, 0.50, or 0.55 to about 0.70 wt % BAE. The retention of the bifenthrin is in the range of from 1.5 to 10.0 grams of bifenthrin per cubic meter of wood, and in another embodiment, in the range of from 2.5 to 9.6 grams of bifenthrin per cubic meter of wood. In further embodiments, the bifenthrin retention is in the range of from about 2.5, 3.0, 3.5, 4.0, 4.5, 5.0, 5.5, 6.0, 6.5, 7.0, 7.5, 8.0, 8.5, or 9.0 to about 10.

In general it is preferred that the composition used to treat the wood, whether in the form of a concentrate or a ready-to-use solution, comprise the borate compound in a wt % BAE in the range of from 0.09 wt % to 12 wt % BAE. Preferred concentrations for pressure treatment applications are in the range of from about 0.3% to 1% BAE. Preferred concentrations for non-pressure applications such as dipping, rolling, spraying, soaking, etc., are in the range of from 3 to 10% BAE.

In general, it is preferred that the bifenthrin be present in the treatment solution at a concentration in the range of from 1 ppm to 5000 ppm. The preferred range of concentrations for pressure treatment applications is from 2 ppm to 100 ppm. For non-pressure applications, the preferred concentration is in the range of from about 500 ppm to 3000 ppm. A treatment solution of a given concentration can be used to give a range of different wood retentions, depending upon the parameters of the method of application. For instance, in the case of pressure applications, such as vacuum and vacuum pressure, varying parameters such as cycle length, vacuum magnitude and pressure magnitude can result in different final wood retentions.

Borate compounds useful in the present composition include Borax, disodiumoctoborate tetrahydrate, Neo Bor, Zinc borates, boric acid, boron oxide, disodiumtetraborate deca and tetrahydrate. Organic borates such as, for example, glycol borates, trimethyl borate and borozoles can be used, as well as other organo-metallic borates. Preferred are disodium octaborate tetrahydrate and boric acid, with disodium octaborate tetrahydrate being most preferred. In the present invention, the retention of borate compounds in the wood or wood product is expressed as boric acid equivalent (BAE). BAE refers to the wt % boric acid which contains the same number of boron atoms as the wt % of the boron compound. Thus, a given wt % BAE corresponds to a wt % boron compound which is dependent upon the identity of the compound.

The compositions of the present invention can be prepared by standard methods. One such method is to dissolve the bifenthrin in a desired solvent in combination with desired emulsifiers to prepare a concentrate, which can be emulsified in an aqueous phase which contains the solvated boron compound. In another embodiment, the borate is dissolved in the aqueous phase after formation of the emulsion. In another embodiment, the bifenthrin is present as a suspension.

The composition of the present invention can be prepared in polar or non-polar solvents, or a mixture of both. The choice of solvent employed generally is dependent upon the solubility properties of the borate compound and bifenthrin and whether a solution or an emulsion is desired, as well as method of application desired. Suitable solvents include water, hydrocarbon solvents of both the aliphatic and aromatic types (such as white spirit, odorless kerosene, diesel oil, light oils, xylene and toluene), oxygenated solvents (such as alcohols, ketones, esters and glycol ethers), and vegetable oils, both processed and natural (such as linseed oil, castor oil and rape seed oil). Blends of oil types may also be used if necessary. The identification of suitable solvents is within the purview of those skilled in the art. In one embodiment, the solvent is a volatile solvent such as water or white spirit. In a preferred embodiment, the solvent is water.

The compositions of the present invention may further comprise additives such as, for example, one or more compounds of the following types: water repellents, pigments, dyes, anti-foaming additives, fire retardants, wetting agents or penetration aids or biocides. Examples of water repellents which can be used include waxes, wax emulsions and silicones. Pigments which can be used, for example, include iron oxide-type pigments and dyes, examples of which include azo dyes, acid dyes and basic dyes. Examples of anti-foaming agents include siloxanes and other oil soluble surfactants. Wetting agents include a wide range of surfactants. Penetration aides, examples of which include chelating agents, imines and surfactants, can be used, if desired. Additives such as resins, non-drying co-solvents, and water repellents can also be included in the present compositions. Examples of biocides include octyl isothiazolin, dichloro octyl isothiazolin, methylisothiazolin, chloromethylisothiazolin, benzisothiazolin, methylene bis thiocyanate, 2 thiocyanomethylthio benzothiazole, and quaternary ammonium compounds such as didecyl dimethyl ammonium chloride, alkylbenzylammonium chloride, saccarine quats, carbo quats such as didecyl dimethyl ammonium carbonate, benzylammonium carbonate.

The composition may be applied to the wood by vacuum impregnation treatments, vacuum-vacuum treatments, hot and cold bath, or by heating the wood and then dipping, soaking, spraying, rolling or brushing, or any other means well known in the art. In a preferred embodiment, vacuum and/or pressure techniques are used to impregnate the wood in accord with this invention including the standard processes, such as the "Empty Cell" process, the "Modified Full Cell" process and the "Full Cell" process, or other vacuum and/or pressure processes known to those skilled in the art.

The standard processes are defined as described in AWPA Standard C1-03 "All Timber Products—Preservative Treatment by Pressure Processes." In the "Empty Cell" process, prior to the introduction of preservative, substrates are subjected to atmospheric air pressure (Lowry) or to higher air pressures (Rueping) of the necessary intensity and duration. In the "Modified Full Cell" process, prior to introduction of preservative, substrates are subjected to a vacuum of less than about 77 kPa (22 inch Hg) (sea level equivalent). A final vacuum of greater than about 77 kPa (22 inch Hg) (sea level equivalent) should be used. In the "Full Cell" process, prior to introduction of preservative or during any period of condition prior to treatment, materials are subjected to a vacuum of greater than about 77 kPa (22 inch Hg). A final vacuum of greater than about 77 kPa (22 inch Hg) is used.

EXAMPLE

*Pinus radiata* D. Don (Radiata pine) specimens (20×20×10 mm long) were cut from the sapwood of several pruned, fast-grown trees that had been harvested from the northern plantation forests of Tasmania, Australia. These samples are referred to as "ensis samples." Trees were 20 to 24 years old. Specimens were pooled and randomly allocated into treatment groups. Prior to treatment, specimens were conditioned to 9.5% moisture content (m.c.). Mean oven-dry density of the specimens was 478 kg/m$^3$.

Solutions of disodium octaborate tetrahydrate and bifenthrin (Determite 100EC) were prepared in the desired concentrations with water as a solvent. The solutions were used immediately.

Twelve specimen groups were treated with the biocide combinations to the retentions indicated in the Table. The following impregnation protocol was used: (the "ensis impregnation protocol"). Specimens were treated by drawing a vacuum of −95 kPa for 30 minutes, introducing the preservative solution while under vacuum, and immediately releasing the vacuum. Specimens were allowed to absorb the solution for 30 minutes atmospheric pressure. Each specimen was weighed before and immediately after treatment to determine retention. The specimens closest to the desired retentions were selected.

Prior to bioassay against termites, all test specimens from each treatment were artificially weathered to H2 conditions by vacuum oven drying for three days at 40° C. and −95 kPa. After removal from the vacuum ovens, the specimens were cooled in a desiccator before being weighed to obtain initial masses. At each stage, care was taken to ensure that specimens of different treatments were kept separate. The weathering step removed from the specimens any volatiles that may be deleterious to termite health and vigor, as well as to provide artificial ageing.

The test specimens were subjected to bioassay in accordance with the minimum requirements specified for H2 conditions in the Australasian Wood Preservation Committee Protocols for Assessment of Wood Preservatives (AWPC 1997), using one species of subterranean termite, *Coptotermes acinaciformis*. *C. acinaciformis* is widely distributed throughout mainland Australia and is responsible for greater economic loss that all other species of Australian termites combined (Gay and Calaby 1970). Only fresh, field collected stocks of termites were used for the bioassay. These termites were collected from the Northern Territory, transported by air to the Ensis Clayton laboratory and used promptly. Six replicate test specimens of each treatment were exposed to termites. A further three specimens were designated as vacuum oven controls.

The following testing protocol was used (the "ensis mean mass loss test").

A single test specimen was centered on a 29 mm plastic disc to stop diffusion of boron out of the specimen. They were centrally placed on a moist matrix of *C. acinaciformis* finely ground mound material (20g, 100% m.c.) within a 250 ml glass jar (96 mm high, 62 mm diameter). Five grams of *C. acinaciformis* were added to each jar. A plastic lid, with a central 9 mm diameter ventilator, closed the jar (FIG. 1). The duration of the bioassay was eight weeks. The bioassay was conducted in an insectary maintained at 27° C., 70% RH.

Three colony sources were incorporated into the experimental design of the bioassay to ensure that variability of vigor and wood consumption exhibited by different colonies of *C. acinaciformis* are taken into account. Hence, two replicate specimens of each treatment (including the controls) were exposed against termites from each of three different colonies (i.e., six replicates per treatment).

At the conclusion of the bioassay, test specimens were removed from the jars and cleaned. The test specimens, as well as vacuum oven controls, were then vacuum oven dried under the same conditions that were used to obtain the initial masses (i.e., 3 days at 40° C. and −95 kPa). After cooling and weighing the specimens, the final and initial masses were compared to obtain mass loss. If necessary, the mass loss of specimens exposed to termites was adjusted to accommodate any changes recorded in the vacuum oven controls.

The results are shown below in the table.

TABLE 1

Target retention, mean actual retention and mean mass loss of test specimens after exposure to *C. acinaciformis* in a laboratory bioassay for eight weeks. Standard errors of the means are given in parentheses.

| Treatment/target retentions (% m/m and g/m³ actives in OD wood) | Mean of actual retentions* | | | Mean mass loss* (%) |
|---|---|---|---|---|
| | BAE (% m/m) | Bifenthrin (g/m³) | Imidacloprid (g/m³) | |
| Water-treated | | | | 99.0 (1.0) |
| 0.1% BAE | 0.106 | | | 93.5 (3.9) |
| 0.2% BAE | 0.213 | | | 30.9 (5.3) |
| 0.5% BAE | 0.540 | | | 48.6 (12.7) |
| 0.1% BAE/2.5 g/m³ bifenthrin | 0.107 | 2.481 | | 7.7 (2.0) |
| 0.1% BAE/5.0 g/m³ bifenthrin | 0.095 | 5.210 | | 5.3 (1.2) |
| 0.1% BAE/7.5 g/m³ bifenthrin | 0.105 | 7.348 | | 2.9 (0.4) |
| 0.2% BAE/2.5 g/m³ bifenthrin | 0.186 | 2.593 | | 5.3 (1.1) |
| 0.2% BAE/5.0 g/m³ bifenthrin | 0.195 | 5.299 | | 3.8 (0.5) |
| 0.2% BAE/7.5 g/m³ bifenthrin | 0.197 | 7.771 | | 2.6 (0.4) |
| 0.5% BAE/2.5 g/m³ bifenthrin | 0.499 | 2.492 | | 3.6 (0.6) |
| 0.5% BAE/5.0 g/m³ bifenthrin | 0.535 | 4.926 | | 1.3 (0.9) |
| 0.5% BAE/7.5 g/m³ bifenthrin | 0.463 | 7.541 | | 2.2 (0.4) |
| 2.5 g/m³ bifenthrin | | 2.506 | | 15.6 (2.9) |
| 5.0 g/m³ bifenthrin | | 4.906 | | 4.8 (0.5) |
| 7.5 g/m³ bifenthrin | | 7.534 | | 4.2 (0.4) |

*mean of 6 replicates

What is claimed is:

1. Wood comprising:
   a) a boron compound having a Boric Acid Equivalent (BAE) retention from greater than 0.15 to 0.7 wt % BAE;
   b) bifenthrin having a retention in the range of from 1.5 to 10.0 grams per cubic meter of wood.

2. Wood as in claim 1 wherein the wood is preserved to a greater extent than wood treated to a BAE retention of 0.15 wt % and a bifenthrin retention in the range of from 1.5 to 10.0 grams per cubic meter of wood as measured by an ensis mean mass loss test protocol.

3. Wood as in claim 1 wherein the boron compound is present at a retention in the range of from 0.2 to 0.7 wt % BAE.

4. Wood as in claim 1 wherein the bifenthrin retention is in the range of from 5.0 to 10.0 grams per cubic meter of wood.

5. Wood as in claim 1 wherein the boron compound is boric acid or a sodium borate compound selected from the group consisting of disodium octaborate tetrahydrate, sodium borate pentahydrate, sodium borate decahydrate and anhydrous borax.

6. A method of preserving wood comprising the steps of:
   a) contacting wood with a solution comprising a boron compound, such that the wood is impregnated with the boron compound to a Boric Acid Equivalent (BAE) retention in a range of from greater than 0.15 to 0.7 wt %;
   b) contacting wood with a solution comprising bifenthrin, such that the wood is impregnated with the bifenthrin to a bifenthrin retention in a range of from 1.5 to 10.0 grams per cubic meter of wood.

7. The method of claim 6 wherein the wood is preserved to a greater extent than wood treated to a BAE retention of 0.15 wt % and a bifenthrin retention in the range of from 1.5 to 10.0 grams per cubic meter of wood as measured by an ensis mean mass loss test protocol.

8. The method of claim 6 wherein the boron compound retention is in the range of from 0.2 to 0.7 wt % BAE.

9. The method of claim 6 wherein the bifenthrin retention is in the range of from 5.0 to 10.0 grams per cubic meter of wood.

10. The method of claim 6 wherein the boron compound solution and the bifenthrin solution is a single solution.

11. The method of claim 6 wherein the boron compound is boric acid or a sodium borate compound selected from the group consisting of disodium octaborate tetrahydrate, sodium borate pentahydrate, sodium borate decahydrate, and anhydrous borax.

12. A composition comprising:
 a) a boron compound; and
 b) bifenthrin;
wherein the composition is a solution; and wherein the solution has a wt % Boric Acid Equivalent (BAE) in the range of from 0.09 to 12, and a bifenthrin concentration in a range of from 1 ppm to 5000 ppm.

13. The composition of claim 12 wherein the boron compound is present at concentration in the range of from 0.3 to 1 wt % BAE.

14. The composition of claim 12 wherein the bifenthrin is present at a concentration in the range of from 2 ppm to 100 ppm.

15. The composition of claim 13 wherein the bifenthrin is present at a concentration in the range of from 2 ppm to 100 ppm.

16. The composition of claim 12 wherein the boron compound is present at a concentration in the range of from 3 to 10 wt % BAE.

17. The composition of claim 12 wherein the bifenthrin is present at a concentration in the range of from 500 ppm to 3000 ppm.

18. The composition of claim 16 wherein the bifenthrin is present at a concentration in the range of from 500 ppm to 3000 ppm.

19. The composition of claim 13 wherein the boron compound is boric acid or a sodium borate compound selected from the group consisting of disodium octaborate tetrahydrate, sodium borate pentahydrate, sodium borate decahydrate, and anhydrous borax.

20. The composition of claim 12 wherein when the solution is applied to ensis samples with an ensis impregnation protocol, the sample has a BAE retention in the range of from 0.15 to 0.7 wt % and a bifenthrin retention in the range of from 1.5 to 10.0 grams per cubic meter of wood.

21. The composition of claim 12 wherein the composition further comprises a water repellent additive selected from the group consisting of waxes, wax emulsions and silicones.

22. The composition of claim 12 wherein the composition further comprises a pigment additive.

23. The composition of claim 22 wherein said pigment additive is selected from the group consisting of iron oxide pigments, dyes, azo dyes, acid dyes and basic dyes.

24. The composition of claim 12 wherein the composition further comprises an anti-foaming agent selected from the group consisting of siloxanes and oil soluble surfactants.

25. The composition of claim 12 wherein the composition further comprises a wetting agent.

26. The composition of claim 25 wherein said wetting agent is a surfactant.

27. The composition of claim 12 wherein the composition further comprises a penetration aide selected from the group consisting of chelating agents, imines and surfactants.

28. The composition of claim 12 wherein the composition further comprises a biocide.

29. The composition of claim 28 wherein the biocide is selected from the group consisting of octyl isothiazolin, dichloro octyl isothiazolin, methylisothiazolin, chloromethylisothiazolin, benzisothiazolin, methylene bis thiocyanate, 2-thiocyanomethylthio benzothiazole, and quaternary ammonium compounds.

30. The composition of claim 29 wherein said quaternary ammonium compounds are selected from the group consisting of didecyl dimethyl ammonium chloride, alkylbenzylammonium chloride, saccarine quats and carbo quats.

31. The composition of claim 30 wherein said carbo quats are selected from the group consisting of didecyl dimethyl ammonium carbonate and benzylammonium carbonate.

\* \* \* \* \*